United States Patent
Sandmeyer et al.

(10) Patent No.: US 11,654,098 B2
(45) Date of Patent: May 23, 2023

(54) PROCESS FOR PREPARING ORGANOPOLYSILOANE GELS

(71) Applicant: WACKER CHEMIE AG, Munich (DE)

(72) Inventors: Frank Sandmeyer, Burgkirchen (DE); Christoph Schosser, Burghausen (DE)

(73) Assignee: WACKER CHEMIE AG, Munich (DE)

( * ) Notice: Subject to any disclaimer, the term of this patent is extended or adjusted under 35 U.S.C. 154(b) by 659 days.

(21) Appl. No.: 16/622,056

(22) PCT Filed: Jun. 12, 2017

(86) PCT No.: PCT/EP2017/064241
§ 371 (c)(1),
(2) Date: Dec. 12, 2019

(87) PCT Pub. No.: WO2018/228657
PCT Pub. Date: Dec. 20, 2018

(65) Prior Publication Data
US 2021/0145727 A1    May 20, 2021

(51) Int. Cl.
| | |
|---|---|
| *A61K 8/899* | (2006.01) |
| *A61K 8/04* | (2006.01) |
| *A61Q 19/00* | (2006.01) |
| *A61K 8/895* | (2006.01) |
| *C08G 77/50* | (2006.01) |
| *C08G 77/08* | (2006.01) |
| *A61K 8/891* | (2006.01) |
| *C08G 77/00* | (2006.01) |

(52) U.S. Cl.
CPC .............. *A61K 8/899* (2013.01); *A61K 8/042* (2013.01); *A61K 8/891* (2013.01); *A61K 8/895* (2013.01); *A61Q 19/00* (2013.01); *C08G 77/08* (2013.01); *C08G 77/50* (2013.01); *A61K 2800/10* (2013.01); *C08G 77/70* (2013.01)

(58) Field of Classification Search
CPC ........ A61K 8/042; A61K 8/891; A61K 8/895; A61K 8/893; A61K 8/89; A61Q 19/00; C08G 77/08; C08G 77/70; C08G 77/12; C08L 83/04

See application file for complete search history.

(56) References Cited

U.S. PATENT DOCUMENTS

| | | |
|---|---|---|
| 5,654,362 A | 8/1997 | Schulz, Jr. et al. |
| 6,200,581 B1 | 3/2001 | Lin et al. |
| 6,423,322 B1 | 7/2002 | Fry |
| 2012/0202895 A1 | 8/2012 | Ikeda |
| 2015/0073059 A1* | 3/2015 | Knoer .................. A61Q 19/008 524/262 |

FOREIGN PATENT DOCUMENTS

DE    102012206209 A1    10/2013

OTHER PUBLICATIONS

Rudolph Heusch, Emulsions, Ullmann's Encyclopedia of Industrial Chemistry, Jun. 15, 2000, pp. 1-58, Wiley-VCH Verlag GmbH & Co., Weinheim, Germany.
DE102012206209, U.S. Equivalent U.S. Pub. No. 2015/073059.

* cited by examiner

*Primary Examiner* — Anna R Falkowitz
(74) *Attorney, Agent, or Firm* — Brooks Kushman P.C.

(57) ABSTRACT

Storage stable organopolysiloxane gels, preparable in commercial quantities are prepared by the hydrosilylation reaction of a silicone resin containing a hydrosilyatable group, a short chain Si—H-functional silicone, and a long chain Si—H-functional silicone.

10 Claims, No Drawings

PROCESS FOR PREPARING ORGANOPOLYSILOANE GELS

CROSS REFERENCE TO RELATED APPLICATIONS

This application is the U.S. National Phase of PCT Appln. No. PCT/EP2017/064241 filed Jun. 12, 2017, the disclosure of which is incorporated in their entirety by reference herein.

BACKGROUND OF THE INVENTION

1. Field of the Invention

The invention relates to a process for producing organopolysiloxane gels and to the use thereof in cosmetic compositions.

2. Description of the Related Art

Organopolysiloxane gels can be produced by crosslinking an unsaturated organopolysiloxane resin with an Si—H-containing organopolysiloxane, also called Si—H-functional crosslinker hereinafter, in the presence of a diluent.

Crosslinks are connections between polymer chains in a three-dimensional network. They may be regarded as long-chain branches that are so numerous that a continuous insoluble network or gel is formed.

Organopolysiloxane networks are frequently produced via platinum-catalyzed hydrosilylation reactions. These frequently involve reaction of an Si—H-containing organopolysiloxane and a vinyl-functional organopolysiloxane. An essential prerequisite for the formation of a 3-dimensional network here is that at least one of the two components, the Si—H-containing organopolysiloxane or the vinyl-functional organopolysiloxane, has more than two functionalities per molecule in the average composition.

The platinum-catalyzed hydrosilylation reaction offers the advantage in the formation of organopolysiloxane networks that no by-products are formed, and that linkage sites and network architecture are tightly defined.

The most important reason for the use of organopolysiloxane gels in cosmetic applications is the sensory advantages achieved thereby, more particularly the improvement in the skinfeel of cosmetic formulations. In addition, organopolysiloxane gels serve as thickeners in cosmetic formulations.

U.S. Pat. No. 6,423,322 B1 discloses organopolysiloxane gels which can be produced easily by hydrosilylation reaction of a specific vinyl-functional MQ resin with an Si—H-containing organopolysiloxane in the presence of a diluent and a small amount of platinum hydrosilylation catalyst in a thermal process, i.e. with heating to a temperature below the boiling point of the diluent used. It is a general characteristic of such hydrosilylation reactions involving MQ resins that they proceed at an acceptable rate to give the desired end product only when they are executed under hot conditions. There is a distinct difference here in the possible heating rates in the laboratory and on the production scale. In the event of a change from one stirrer system to another, differences of this kind generally recur when the stirrer systems differ with regard to their size, material characteristics or technical design. It has been found that the achievable viscosities of such MQ resin-containing gels are dependent on the heating rate. The higher the heating rate, the higher the achievable viscosity for a given composition and for a fixed concentration of gel in the diluent. Both the concentration of film-forming gel or active ingredient and the viscosity, have a distinct effect on the skinfeel of a cosmetic formulation for skincare.

U.S. Pat. No. 5,654,362 teaches silicone gels for cosmetic applications that are obtained by hydrosilylation reactions of alpha,omega-dienes with terminally and/or pendently Si—H-functional linear polyorganosiloxanes. The hydrosilylation takes place using a suitable catalyst in a solvent, which may itself be a polyorganosiloxane.

A common factor in these processes is that the crosslinked gel structures are formed by the use of an Si—H-containing component and a vinyl-functional component. The means of controlling the product property of viscosity both during the production and in later use are thus restricted to the selection of the respective raw materials and the amount of the respective diluent or solvent. The point at which this restriction is problematic is when invariable boundary conditions are encountered, as can occur, for example, in the event of changes in scale from laboratory scale to the production scale. Such boundary conditions may especially be limited heating rates.

A changeover in the formulation, for example as a result of the complete exchange of one component for another and alignment with the altered starting position generally results in very substantial changes in the product properties, such that an increase in scale of the target product becomes an insoluble problem. Instead, attempts have to be made with considerable effort to develop a product with the same performance at a larger scale.

US 2012/0202895 A1 teaches a pasty formulation for cosmetic applications obtained by the hydrosilylation of one or more Si—H-containing polyorganosiloxanes with one or more aliphatically unsaturated polyorganosiloxanes in an oil which is liquid at 25° C. as solvent. In this case, the polyorganosiloxanes used are exclusively linear polyorganosiloxanes, not resins. At least two of the polyorganosiloxanes from the group of the Si—H-containing and unsaturated linear polyorganosiloxanes must have a chain length of more than 30 repeat units in order that no oily, greasy skinfeel occurs in the application. The viscosity of the polyorganosiloxane pastes thus obtained is the same in all examples, irrespective of the chain lengths of the Si—H-containing polyorganosiloxanes used, i.e. also irrespective of whether two of the Si—H-containing polyorganosiloxanes have a chain length of more than 30 or not. Thus, although US 2012/0202895 A1 discloses the option of controlling the sensory properties of an elastomer gel, it does not disclose any way of controlling the viscosity thereof.

The problem addressed was that of providing a simple process for controlling the viscosity of organopolysiloxane gels that permits the transfer of the process to various apparatuses, for example in the event of increases in scale, especially the transfer of the process under altered boundary conditions, such as reduction in the heating rate, with retention of the sensory properties of the organopolysiloxane gels with minimum adjustments to the formulation.

The foregoing problem is solved by the invention.

SUMMARY OF THE INVENTION

Organopolysiloxane gels are produced by a process of reacting MQ resins having aliphatic unsaturation, optionally compounds having a polar organic group, a mixture of Si—H functional organopolysiloxanes, a diluent, and optionally a reaction terminator.

DETAILED DESCRIPTION OF THE PREFERRED EMBODIMENTS

The organopolysiloxane gels are preferably produced by reacting (1a) unsaturated organopolysiloxane resins composed of units of the formulae $SiO_2$ (Q units) and $R_3SiO_{1/2}$ and $R_2R^1SiO_{1/2}$ (M units), where R may be the same or different and is a monovalent, optionally substituted hydrocarbon radical having 1 to 18 carbon atoms per radical, $R^1$ is a monovalent hydrocarbon radical onto which Si—H groups may be added in a hydrosilylation reaction, preferably a monovalent hydrocarbon radical which has a terminal aliphatic C—C multiple bond and has 2 to 18 carbon atoms, more preferably an ω-alkenyl radical having 2 to 12 carbon atoms, especially a vinyl radical, with the proviso that the organopolysiloxane resins contain at least 2 $R^1$ radicals, preferably at least 3 $R^1$ radicals, and that the molar ratio of M units to Q units is in the range from 0.5 to 4.0, preferably in the range from 0.5 to 2.0. The organopolysiloxane resins may contain, in addition to the M and Q units, small amounts of $RSiO_{3/2}$ (T) units or $R_2SiO_{2/2}$ (D) units, preferably in amounts of 0.01 to 20 mol %, based on the sum total of all siloxane units, and the organopolysiloxane resins may contain up to 10% by weight of free Si-bonded hydroxyl or alkoxy groups, and optionally (1b) compounds having a polar organic group, preferably glycoside group, such as an oligo- or polysaccharide group, a polyoxyalkyl group such as a polyoxyethylene or polyoxypropylene group, a hydroxyl, amide or carboxyl group, and a hydrosilylatable end group, with (2) a mixture of two Si—H-containing organopolysiloxanes which have different average chain lengths and are of the formula

$$(R^2{}_{3-x}H_xSiO_{1/2})\,(R^2{}_2SiO_{2/2})_a(R^2HSiO_{2/2})_b(R^2{}_{3-x}H_x\text{-}SiO_{1/2}) \quad (I)$$

where $R^2$ is the same or different and is an unsubstituted or optionally heteroatom-substituted, aliphatic, cycloaliphatic or aromatic, optionally polycyclic, $C_1$-$C_{18}$ hydrocarbon radical, x is 0 or 1, a and b are each integers≥0, with the proviso that the sum total of a+b≥30, that the organopolysiloxanes contain an average of at least 2 Si-bonded hydrogen atoms, preferably at least 3 Si-bonded hydrogen atoms, and that the long-chain organopolysiloxane of the two organopolysiloxanes has at least 3 times the chain length (a+b) of the short-chain organopolysiloxane, in the presence of (3) catalysts that promote the addition of Si-bonded hydrogen onto aliphatic multiple bonds, where (1a), optionally (1b) and (2) are dispersed in (4) diluents, preferably organopolysiloxanes having 2 to 200 silicon atoms, preferably 2 to 50 silicon atoms, or organic diluents or mixtures of organopolysiloxanes having 2 to 200 silicon atoms, preferably 2 to 50 silicon atoms, and organic diluents, and the reaction is stopped by addition of (5) stopper compounds used as catalyst poisons.

It has been found that, surprisingly, the use of Si—H-containing organopolysiloxanes of different chain lengths opens up an effective measure for controlling the viscosity of organopolysiloxane gels. This was not to be expected from US 2012/0202895 A1.

The unsaturated organopolysiloxane resins (1a) preferably have a viscosity greater than 0.7 mm²/s at 25° C. Preference is given to those organopolysiloxane resins which have a viscosity of greater than 1000 mm²/s at 25° C., or which are solids. The weight-average molecular weight Mw determined by gel permeation chromatography (based on a polystyrene standard) of these organopolysiloxane resins is preferably 334 to 200,000 g/mol, preferably 1000 to 20,000 g/mol.

The unsaturated organopolysiloxane resins (1a) preferably have an iodine number less than 254, more preferably an iodine number less than 76.

Compounds (Ib) can be used in order to impart specific properties to the organopolysiloxane gels, for instance hydrophilicity and water swellability.

Preferred compounds (Ib) are those that contain a glycoside group, such as oligo- or polysaccharide group, or a polyoxyalkyl group, such as polyoxyethylene or polyoxypropylene group, and have a hydrosilylatable end group.

Compounds (Ib) are preferably used in such amounts that they are present in a proportion by weight, based on the total weight of the organopolysiloxane gel obtained, of 0.1% to 10% by weight.

Such gels have improved compatibility with polar organic substances and are even capable of absorbing extremely hydrophilic liquids such as water or glycerol without losing the viscous gel structure.

In the context of this invention, the formula (I) for the Si—H-containing organopolysiloxanes should be understood such that the units of the formulae $(R^2{}_2SiO_{2/2})_a$ and $(R^2HSiO_{2/2})_b$ may be distributed in any manner in the organopolysiloxane molecule, meaning that either identical units may follow on from one another in blocks or that there may be a more or less random sequence of the units with any alternation.

The Si—H-containing organopolysiloxanes of formula (I) contain Si-bonded hydrogen in amounts of 0.010% by weight to 1.60% by weight, preferably 0.010-1.30% by weight, more preferably 0.010-1.25% by weight, and especially 0.010-0.60% by weight, where the amounts of Si-bonded hydrogen for the two Si—H-containing organopolysiloxanes of different length may but need not be different. If the amounts of Si-bonded hydrogen are different for the two Si—H-containing organopolysiloxanes of different length, there is no preference for which of the two Si—H-containing organopolysiloxanes of different length contains the greater or smaller amount of Si-bonded hydrogen.

The Si-bonded hydrogen atoms in formula (I) may be bonded either solely to the terminal silicon atoms, solely to the catenated silicon atoms, or both to the catenated and to the terminal silicon atoms.

The $R^2$ radical in formula (I) excludes heteroatoms that would hinder the hydrosilylation reaction, such as nitrogen and sulfur atoms.

Preferably, in formula (I), the sum of a+b≥40; more preferably, the sum of a+b≥55.

Preferably, the long-chain of the two organopolysiloxanes in (2) has at least 3.1 times the chain length (a+b), more preferably 3.2 times the chain length, and especially 3.4 or more times the chain length, of the short-chain organopolysiloxane.

Examples of R radicals are alkyl radicals such as the methyl, ethyl, n-propyl, isopropyl, 1-n-butyl, 2-n-butyl, isobutyl, tert-butyl, n-pentyl, isopentyl, neopentyl, and tertpentyl radicals, hexyl radicals such as the n-hexyl radical, heptyl radicals such as the n-heptyl radical, octyl radicals such as the n-octyl radical and isooctyl radicals such as the 2,2,4-trimethylpentyl radical, nonyl radicals such as the n-nonyl radical, decyl radicals such as the n-decyl radical, dodecyl radicals such as the n-dodecyl radical, and octadecyl radicals such as the n-octadecyl radical; cycloalkyl radicals such as cyclopentyl, cyclohexyl, cycloheptyl and methylcyclohexyl radicals; aryl radicals such as the phenyl, naphthyl, anthryl and phenanthryl radical; alkaryl radicals such as o-, m-, p-tolyl radicals, xylyl radicals and ethylphenyl radicals; and aralkyl radicals such as the benzyl radical, the α- and the β-phenylethyl radical.

Examples of substituted R radicals are haloalkyl radicals such as the 3,3,3-trifluoro-n-propyl radical, the 2,2,2,2',2',2'-hexafluoroisopropyl radical, the heptafluoroisopropyl radical and haloaryl radicals such as the o-, m- and p-chlorophenyl radical.

Examples of R radicals are fully applicable to $R^2$ radicals.

Preferably, the R radical and the $R^2$ radical are a monovalent hydrocarbyl radical having 1 to 6 carbon atoms, particular preference being given to the methyl radical.

Examples of $R^1$ radicals are alkenyl radicals such as the vinyl, 5-hexenyl, cyclohexenyl, 1-propenyl, allyl, 3-butenyl and 4-pentenyl radical, and alkynyl radicals such as the ethynyl, propargyl and 1-propynyl radical. Preferably, the $R^1$ radicals are alkenyl radicals, especially preferably ω-alkenyl radicals, more particularly the vinyl radical.

In the process for preparing the organopolysiloxane gels of the invention, unsaturated organopolysiloxane resins (1a) and optionally compounds (1b) are preferably used in amounts of 4.5 to 0.1 mol, more preferably 2 to 0.8 mol, especially 1.8 to 1.1 mol of hydrocarbon radical having aliphatic C—C-multiple bond per mole of Si-bonded hydrogen in the Si—H-containing organopolysiloxanes (2).

The gels of the invention have excellent skinfeel. It has been found that, surprisingly, when the process of the invention is employed, control of the viscosity of the organopolysiloxane gels is possible via the variation of the mixing ratio of the two Si—H-containing organopolysiloxanes of different length. What this means is, more particularly, that given constant concentration of the organopolysiloxane gel network and given otherwise identical reaction conditions in the synthesis of the organopolysiloxane gels, i.e. given identical procedure, at identical temperature and with an identical temperature regime, with identical metering rates, etc., a greater amount of the longer Si—H-containing organopolysiloxane leads to a higher viscosity of the respective gel. If the reaction conditions are varied, this effect is maintained. As will be shown later in the examples, this means that, when the viscosity of an organopolysiloxane gel is reduced by the reduction in the heating rate, the viscosity of the organopolysiloxane gel containing a higher proportion of longer-chain H-siloxane is still higher than the viscosity of the organopolysiloxane gel having the higher proportion of shorter-chain H-siloxane. This achieves the effect underlying the object of the invention, that it is possible to establish a particular target viscosity even in the event of a variation in the reaction conditions that affects the viscosity without making any such significant change to the chemistry of the organopolysiloxane network that it fundamentally alters the organopolysiloxane gel and its properties. In fact, it has been found that the use properties of organopolysiloxane gels, upon variation of the ratio of the two H-siloxanes of different length, differ so marginally that they are usable in a performance-equivalent manner. Before the comparison of the performance properties, it should always be ensured that the organopolysiloxane gels to be compared, if necessary, are adjusted to the same viscosity by the addition of diluents since the viscosity itself has a considerable influence on the skinfeel to be established. This effect therefore has to be excluded before the properties of the two organopolysiloxane gels are compared.

It should also be noted in this connection that the respective solids content of the organopolysiloxane gel affects the application properties. The solids content here is the concentration of the organopolysiloxane gel network which is obtained from the hydrosilylation reaction in the diluent. In principle, the viscosity of an organopolysiloxane gel can also be increased via the increase in the solids content without making any change in the chemistry of the hydrosilylation reaction. However, this is again at the expense of the application properties. When the process of the invention is employed in the case of a variation in reaction conditions which affects the viscosity, for example the heating rate, the target viscosity is attained by the adjustment of the ratio of the two different H-siloxanes, keeping the solids content of the organopolysiloxane gel constant.

An essential requirement for all of this to be possible is that the difference in chain length between the two H-siloxanes is sufficiently great.

It has been found that the chain length of the longer-chain H-siloxane has to be at least 3 times the chain length of the shorter-chain H-siloxane, where the chain length of the shorter-chain H-siloxane is preferably at least 40, and especially at least 55 siloxane units a+b in formula (I).

In the context of the experimental studies, for example, the combination of two H-siloxanes having the chain lengths of 75 and 225 and of 140 and 450 has been found to be particularly effective.

Particularly effective H-siloxanes of the formula (I) were those that contained solely catenated Si—H units b and x=0, i.e. those of the formula (I'):

$$(R^2{}_3SiO_{1/2})(R^2{}_2SiO_{2/2})_a(R^2HSiO_{2/2})_b(R^2{}_3SiO_{1/2}) \quad (I')$$

where $R^2$, a and b are as defined above.

Examples of preferred short-chain H-siloxanes are those for which the $R^2$ radicals in formula (I') are methyl radicals and in which the a:b ratio has the values specified in table 1 below:

TABLE 1

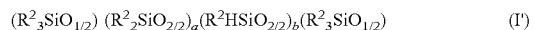

| Serial number | Distribution a:b | Chain length (a + b) |
|---|---|---|
| 1 | a = 0 | 55 |
| 2 | 0.3:1 | 45 |
| 3 | 0.5:1 | 60 |
| 4 | 1:1 | 140 |
| 5 | 2:1 | 140 |
| 6 | 3.5:1 | 45 |
| 7 | 5:1 | 75 |
| 8 | 6:1 | 65 |
| 9 | 7:1 | 80 |
| 10 | 9:1 | 60 |
| 11 | 15:1 | 75 |
| 12 | 20:1 | 75 |
| 13 | 25:1 | 85 |
| 14 | 50:1 | 140 |

Examples of preferred long-chain H-siloxane equilibrates are those for which the $R^2$ radicals in formula (I') are methyl radicals, and in which the a:b ratio has the values specified in table 2 below:

TABLE 2 long-chain Si—H-containing polydimethylsiloxanes

| Serial number | Distribution a:b | Chain length (a + b) |
|---|---|---|
| 15 | a = 0 | 255 |
| 16 | 0.3:1 | 225 |
| 17 | 0.5:1 | 360 |
| 18 | 1:1 | 440 |
| 19 | 2:1 | 275 |
| 20 | 3.5:1 | 365 |
| 21 | 5:1 | 445 |
| 22 | 6:1 | 360 |
| 23 | 7:1 | 375 |
| 24 | 9:1 | 465 |
| 25 | 15:1 | 225 |
| 26 | 20:1 | 465 |
| 27 | 25:1 | 365 |
| 28 | 50:1 | 450 |

Catalysts (3) used in the process of the invention may be the same catalysts which are useful to promote the addition of Si-bonded hydrogen onto aliphatic multiple bonds. The catalysts are preferably a metal from the group of the platinum metals or a compound or a complex from the group of the platinum metals. Examples of such catalysts are metallic and finely divided platinum, which may be present on supports such as silicon dioxide, aluminum oxide or activated carbon, compounds or complexes of platinum, such as platinum halides, e.g. $PtCl_4$, $H_2PtCl_6 \cdot 6H_2O$, $Na_2PtCl_4 \cdot 4H_2O$, platinum-olefin complexes, platinum-alcohol complexes, platinum alkoxide complexes, platinum-ether complexes, platinum-aldehyde complexes, platinum-ketone complexes, including reaction products formed from $H_2PtCl_6 \cdot 6H_2O$ and cyclohexanone, platinum-vinylsiloxane complexes such as platinum-1,3-divinyl-1,1,3,3-tetramethyldisiloxane complexes with or without a content of detectable inorganically bound halogen, bis(γ-picoline)-platinum dichloride, trimethylenedipyridineplatinum dichloride, dicyclopentadieneplatinum dichloride, (dimethyl sulfoxide)ethyleneplatinum(II) dichloride, cyclooctadiene-platinum dichloride, norbornadieneplatinum dichloride, γ-picolineplatinum dichloride, cyclopentadieneplatinum dichloride, and reaction products of platinum tetrachloride with olefin and primary amine or secondary amine or primary and secondary amine, such as the reaction product of platinum tetrachloride dissolved in 1-octene with sec-butylamine or ammonium-platinum complexes. Preferred hydrosilylation catalysts are platinum compounds present in a solvent suitable for use in cosmetic formulations.

Preferably, the catalyst (3) is used in amounts of 1 to 100 ppm by weight (parts per weight per million parts by weight), calculated as elemental platinum and based on the total weight of components (1a), optionally (1b) and (2).

It has been found that an excessively large amount of platinum catalyst has an adverse effect on the sensory properties of the organopolysiloxane gels obtained. More particularly, the property of crumbliness is adversely affected. Moreover, too great an amount of platinum catalyst promotes a disadvantageous yellow color of the gels, quite apart from the fact that the use of a larger amount of platinum than absolutely required entails economic drawbacks owing to the high cost of such catalysts. Therefore, an amount of more than 100 ppm by weight of elemental platinum, based on the total weight of components (1a), optionally (1b) and (2), is preferably ruled out, even though the process leads in principle to organopolysiloxane gels even with greater amounts of platinum. However, since these are only of very limited benefit, if any, for the target field of use of cosmetics, their inclusion in the scope of the invention is not preferred.

It has been found, more particularly, that greater amounts of platinum catalyst are required for hydrosilylation reactions that proceed with employment of heat than for those hydrosilylations that proceed even at room temperature, i.e. at 20-30° C., without the employment of externally supplied heat. For hydrosilylations with employment of heat, amounts of platinum of 10-90 ppm by weight, particularly of 15-80 ppm by weight and especially of 20-75 ppm by weight have been found to be advantageous. For reactions that proceed even under "cold" conditions, i.e. at room temperature and heat up of their own accord solely via the evolution of exothermic heat of reaction, amounts of platinum of 1-60 ppm by weight, particularly of 2-55 ppm by weight, especially of 3-50 ppm by weight, have been found to be advantageous and sufficient.

The organopolysiloxane gels of the invention preferably contain 1% to 98% by weight of diluent, preferably 50% to 95% by weight of diluent, based on the total weight of the organopolysiloxane gels.

Unreactive or relatively unreactive diluents are preferred. In the context of the present invention, the term "unreactive" is used in relation to the crosslinking reaction in question and the reactants used therein. A relatively unreactive diluent is less than one tenth as reactive with the reactants of the crosslinking reaction as compared with the reactants with one another in the crosslinking reaction.

Suitable examples of diluents include cyclic and linear organopolysiloxanes, organic diluents or mixtures of organopolysiloxanes and organic diluents.

The organopolysiloxane used as diluent may be a single organopolysiloxane or a mixture of organopolysiloxanes. The organopolysiloxane may bear alkyl, aryl, alkaryl and aralkyl groups. Such organopolysiloxanes may be specified by way of example by polydimethylsiloxane, polydiethylsiloxane, polymethylethylsiloxane, polymethylphenylsiloxane and polydiphenylsiloxane, but are not limited thereto.

Another possibility is the use of functional organopolysiloxanes as diluent, for example acrylamide-functional siloxane fluids, acryloyl-functional siloxane fluids, amide-functional siloxane fluids, amino-functional siloxane fluids, carbinol-functional siloxane fluids, carboxy-functional siloxane fluids, chloroalkyl-functional siloxane fluids, epoxy-functional siloxane fluids, glycol-functional siloxane fluids, ketal-functional siloxane fluids, mercapto-functional siloxane fluids, methyl ester-functional siloxane fluids, perfluoro-functional siloxane fluids and silanol-functional siloxanes.

Cyclic polydimethylsiloxanes as diluent may by way of example be hexamethylcyclotrisiloxane, octamethylcyclotetrasiloxane, decamethylcyclopentasiloxane and dodecamethylcyclohexasiloxane, but are not limited thereto.

Preferably, the organopolysiloxanes used as a diluent are polydimethylsiloxanes having 2 to 200 silicon atoms, preferably 2 to 50 silicon atoms, with particular preference being given to linear polydimethylsiloxanes having a viscosity of 1.5 to 50 mm²/s at 25° C.

Organic diluents used may be aromatic hydrocarbons, alcohols, aldehydes, ketones, amines, esters, ethers, alkyl halides or aromatic halides. Representative examples are alcohols such as methanol, ethanol, i-propanol, cyclohexanol, benzyl alcohol, 2-octanol, ethylene glycol, propylene glycol and glycerol; aliphatic hydrocarbons such as pentane, cyclohexane, heptane, paint benzines; alkyl halides such as chloroform, carbon tetrachloride, perchloroethylene, ethyl chloride and chlorobenzene; aromatic hydrocarbons such as benzene, toluene, ethyl benzene and xylene; esters of carboxylic acids having 2 to 30 carbon atoms, such as ethyl acetate, isopropyl acetate, ethyl acetoacetate, amyl acetate, isobutyl isobutyrate, benzyl acetate, isopropyl palmitate and isopropyl myristate; ethers such as ethyl ether, n-butyl ether, tetrahydrofuran and 1,4-dioxane; ketones such as acetone, methyl ethyl ketone, cyclohexanone, diacetone alcohol, methyl amyl ketone and diisobutyl ketone; fatty oils including polyunsaturated ω-3- and ω-6-fatty acids, and esters thereof; vegetable oils such as peanut, olive, palm, canola, maize kernel, soya and sunflower oil and the like; and natural and synthetic oils or oil-soluble solids, such as various mono-, di- and triglycerides, polyalkoxylated vegetable oils, lanolin, lecithin and the like; and mineral oil hydrocarbons such as petrolatum, mineral oil, benzine, petroleum ether. These examples serve for illustration and should not be regarded as a restriction.

Other mixed organic diluents may likewise be used, such as acetonitrile, nitromethane, dimethylformamide, propylene oxide, trioctyl phosphate, butyrolactone, furfural, pine oil, turpentine and m-cresol.

Suitable organic diluents are also volatile flavoring substances such as peppermint oil, spearmint oil, menthol, vanilla, cinnamon oil, clove oil, bay oil, anise oil, eucalyptus oil, thyme oil, cedar oil, nutmeg oil, sage oil, cassia oil, cocoa, liquorice juice, starch sugar syrup from corn having a high fructose content, citrus oils such as lemon, orange, lime and grapefruit, fruit essences such as apple, pear, peach, grape, strawberry, raspberry, cherry, plum, pineapple and apricot; and other useful flavoring substances including aldehydes and esters, such as ethyl cinnamate, cinnamaldehyde, eugenyl formate, p-methylanisole, acetaldehyde, benzaldehyde, anisaldehyde, citral, neral, decanal, vanillin, tolylaldehyde, 2,6-dimethyloctanal and 2-ethylbutyraldehyde.

A portion of or the entire organic diluent may include one or more volatile fragrances, such as natural products and perfume oils. Some representative natural products and perfume oils are amber, benzoin, civet, clove, cedar oil, jasmine, maté, mimosa, musk, myrrh, iris, sandalwood oil and vetiver oil; aroma chemicals such as amyl salicylate, amylcinnamaldehyde, benzyl acetate, citronellol, coumarin, geraniol, isobornyl acetate, ambrette and terpinyl acetate, and various classic perfume oil families such as the flower bouquet family, the oriental family, the chypre family, the wood family, the citrus family, the canoe family, the leather family, the spice family and the herb family.

The organic diluent may also include aliphatic or alicyclic hydrocarbons having 4 to 30 carbon atoms, preferably saturated hydrocarbons. The aliphatic hydrocarbons may be straight-chain or branched, and the alicyclic hydrocarbons may be unsubstituted cyclic hydrocarbons or aliphatic hydrocarbyl-substituted hydrocarbons. Examples of suitable hydrocarbons are n-heptane, n-octane, isooctane, n-decane, isodecane, n-dodecane, isododecane, cyclohexane, cycloheptane, cyclooctane, methylcyclohexane, dimethylcyclohexane, ethylcyclohexane, nonylcyclohexane and the like. This enumeration too serves for elucidation and should not be regarded as a restriction.

Further suitable organic diluents are oil-like polyethers such as bis(alkyl) ethers of low molecular weight glycols, and liquid oligomeric and polymeric polyoxyalkylene glycols, and the alkyl mono- and diethers and mono- and dialkyl esters thereof, but the use thereof is not preferred. Preferably, the predominant portion of the polyoxyalkylene glycols is produced from a predominant portion (>50 mol %) of alkylene oxides having more than two carbon atoms, i.e. propylene oxide, 1,2- and 2,3-butylene oxide, tetrahydrofuran, oxetane, cyclohexene oxide and the like.

Preferred organic diluents have a viscosity in the range from 0.5 to 200 mm$^2$/s (25° C.), particular preference being given to those diluents having a boiling point in the range from 50° C. to 300° C.

It is possible to use numerous mixtures of diluents restricted solely to those compositions where no phase separation occurs after the production of the organopolysiloxane gel of the invention.

The production of the gel is easy to perform. In general, all constituents apart from the catalyst are added in a one-pot process, the mixture is stirred gradually until the possibly pulverulent unsaturated organopolysiloxane resin has dissolved, and then the catalyst is added while stirring continuously. The composition can be left at room temperature until a gel has formed, or it can be heated.

Preferably, the composition is heated to a temperature between 50° C. and 130° C., preferably between 70° C. and 120° C., until the mixture gels or solidifies. The gelation preferably proceeds within ten hours, more preferably within three hours.

The reaction is preferably stopped at the end of the reaction time by adding a hydrosilylation catalyst poison as a stopper compound (5), which ends the further curing which is brought about by remaining crosslinking hydrosilylation reactions that occur in the silicone elastomers. Stoppers used here are catalyst poisons that irreversibly alter and hence deactivate the hydrosilylation catalyst.

The stopper compounds (5) are preferably used in amounts of at least 1.1 mol of functional group that brings about the stopping, preferably a mercapto group, per mole of elemental platinum in the catalyst (3).

It has been found here to be particularly advantageous to use a distinctly superstoichiometric amount of the stopper since this has a positive effect on the long-term retention of the creaminess of the finished gel.

Examples of stopper compounds (5) suitable for ending the further curing are organosulfur compounds such as organic compounds having mercapto groups. Further suitable compounds are mentioned in U.S. Pat. No. 6,200,581. Preferred hydrosilylation catalyst poisons as stopper compounds (5) are organopolysiloxanes having mercaptoalkyl groups, particular preference being given to organopolysiloxanes having 3-mercaptopropyl groups, such as mercaptopropyl-functional silsesquisiloxanes or mercaptopropyl-functional polyorganosiloxanes.

Organopolysiloxanes having mercaptoalkyl groups that are used as stopper compounds (5) are preferably used in amounts of 200 to 1.1 mol, more preferably 50 to 1.5 mol, especially preferably 20 to 2.0 mol, of mercapto groups per mole of elemental platinum in the catalyst (3).

The process of the invention affords organopolysiloxane gels suitable for use in cosmetic formulations.

It is also possible to execute the process in two component steps, in which case the hydrosilylation with the first of the two Si—H-containing organopolysiloxanes of different length takes place essentially in the first component step, and the hydrosilylation with the second Si—H-containing organopolysiloxane in the second component step. In principle, it is unimportant whether the short-chain or long-chain Si—H-containing organopolysiloxane is used first for hydrosilylation, but it is preferable that hydrosilylation is effected with the short-chain Si—H-containing organopolysiloxane in the first component step and with the long-chain Si—H-containing organopolysiloxane in the second component step. Since the short-chain Si—H-containing organopolysiloxane results in a lower-viscosity precursor, it is easier in the preferred procedure to disperse the second Si—H-containing organopolysiloxane homogeneously in the second component step.

The procedure in the process in component steps differs from the procedure in the one-pot process in that not the entire mass of all reactants is used from the start. First of all, the Si—H-containing organopolysiloxane used first, preferably the short-chain Si—H-containing organopolysiloxane, is mixed with the entire amount of the unsaturated organopolysiloxane resin (1a) and the diluent (4). If a pulverulent unsaturated organopolysiloxane resin is used, it is either dissolved in a diluent beforehand or it is added to the reaction mixture in pulverulent form and dispersed until the resin has dissolved completely.

Subsequently, the catalyst is added with continuous stirring. In this case, it is possible to add either the entire amount of catalyst required for the reaction or just a portion thereof. Preference is given to heating to a temperature between 50° C. and 130° C., preferably between 70° C. and 120° C., until the mixture gels or solidifies. The gelation preferably takes place within ten hours, preferably within three hours.

Thereafter, in the second component step of the gel production, the second Si—H-containing organopolysiloxane, preferably the long-chain Si—H-containing organopolysiloxane, is added while stirring. If the entire amount of catalyst has not yet been added, the remainder of the amount of catalyst required is then added and stirring is continued until the mixture gels or solidifies. The gelation preferably takes place within ten hours, preferably within three hours. The reaction is stopped at the end of the reaction time by adding a stopper as already set out further up. Organopolysiloxane gels suitable for use in cosmetic formulations are obtained.

Optionally, according to the process chosen, the organopolysiloxane base gel obtained at first can be diluted in a second or third optional process step.

This is done using high-shear mixing techniques according to the prior art.

The diluting can be effected by intensive mixing and dispersing with suitable stirrer equipment or in rotor-stator stirring apparatus, colloid mills, high-pressure homogenizers, microchannels, membranes, jet nozzles and the like, or by means of ultrasound. This involves using homogenizing equipment and processes according to the prior art. Homogenizing equipment and methods are described, for example, in Ullmann's Encyclopedia of Industrial Chemistry, CD-ROM edition 2003, Wiley-VCH Verlag, under the heading "Emulsions".

In the optional step of diluting the organopolysiloxane base gel, it is possible to produce a multitude of different gels which vary within a wide range in terms of their consistency and their profile of properties. It is possible to use the same diluent which has been used in the first process step or the first two process steps, or a second diluent different therefrom. Alternatively, it is also possible to add any desired mixture of the diluents described previously herein and/or an active ingredient for personal care or healthcare or a mixture of an active ingredient for personal care or healthcare with one or more of the diluents described herein, with the proviso that no phase separation occurs.

An "active ingredient for personal care or healthcare" in the present context means any compound or mixture of compounds which are known in the technical field as additives in personal care formulations and which are typically added in order to treat the hair or skin, in order to achieve a cosmetic and/or esthetic benefit; any compound or mixture of compounds which are known in the field in order to achieve a pharmaceutical or medical benefit; any compound with which pharmacological efficacy or any other effect in diagnosis, healing, alleviation, treatment or prevention of diseases is to be achieved, or in order to influence the structure or any function of the human or animal body; and any compound which can undergo a chemical change in the production of medicament products and which can be present in modified form in medicaments, in order to cause the specified efficacy or the specified effect.

The active ingredients for personal care or healthcare are preferably selected from the group of the fat- or oil-soluble vitamins, oil-soluble medicaments, antiacne agents, antibacterial agents, fungicides, inflammation inhibitors, dandruff control agents, narcotics, pruritus-relieving agents, skin inflammation inhibitors and agents which are generally considered to be barrier films, and oil-soluble UV absorbers.

Examples of useful active constituents for use in the optional third process step according to the invention are as follows:

Examples of oil-soluble vitamins include, but are not limited to, vitamin $A_1$, RETINOL, $C_2$ to $C_{18}$ esters of RETINOL, vitamin E, TOCOPHEROL, esters of vitamin E and mixtures thereof. RETINOL includes trans-RETINOL, 13-cis-RETINOL, 11-cis-RETINOL, 9-cis-RETINOL and 3,4-didehydro-RETINOL. The oil-soluble vitamin may be used in the composition according to the invention in amounts of 0.01 to 50 percent by weight.

It should be noted that RETINOL is an International Nomenclature Cosmetic Ingredient Name (INCI), conferred by The Cosmetic, Toiletry and Fragrance Association (CTFA), Washington D.C., for vitamin A. Other suitable vitamins and the INCI names for the vitamins in question which are included herein are RETINYL ACETATE, RETINYL PALMITATE, RETINYL PROPIONATE, a-α-TOCOPHEROL, TOCOPHERSOLAN, TOCOPHERYL ACETATE, TOCOPHERYL LINOLEATE, TOCOPHERYL NICOTINATE and TOCOPHERYL SUCCINATE.

Some examples of commercially available products suitable for use herein are vitamin A acetate, Fluka Chemie AG, Buchs, Switzerland; CIOVI-OX T-50, a vitamin E product from Henkel Corporation, La Grange, Ill.; COVI-OX T-70, another vitamin E product from Henkel Corporation, La Grange, Ill., and vitamin E acetate, a product from Roche Vitamins & Fine Chemicals, Nutley, N.J.

Representative examples of some suitable oil-soluble medicaments which can be added as active constituents are clonidine, scopolamine, propranolol, estradiol, phenylpropanolamine hydrochloride, ouabain, atropine, haloperidol, isosorbide, nitroglycerine, ibuprofen, ubiquinone, indomethacin, prostaglandins, naproxen, salbutamol, guanabenz, labetalol, pheniramine, metrifonate and steroids.

Likewise encompassed herein as a medicament for the purposes of the present invention are antiacne agents such as benzoyl peroxide, triclosan and tretinoin; antibacterial agents such as chlorhexidine gluconate; fungicides such as miconazole nitrate; inflammation inhibitors such as salicylic acid; corticosteroidal medicaments; non-steroidal inflammation inhibitors such as diclofenac; dandruff control agents such as clobetasol propionate and retinoids, narcotics such as lidocaine; pruritus-relieving agents such as polidocanol; skin inflammation inhibitors such as prednisolone, and agents which are generally regarded as barrier films.

Representative examples of oil-soluble UV absorbers which can be added as active constituents are 1-(4-methoxyphenyl)-3-(4-tert-butylphenyl)propane-1,3-dione (INCI:

Butyl Methoxydibenzoylmethane), 2-ethylhexyl (2E)-3-(4-methoxyphenyl)prop-2-enoate (INCI: Octyl Methoxycinnamate), 4-hydroxy-2-methoxy-5-(oxophenylmethyl)benzenesulfonic acid (INCI: Benzophenone-4), 2-hydroxy-4-methoxybenzophenone-5-sulfonic acid sodium salt (INCI: Benzophenone-5) and 2-ethylhexyl 2-hydroxybenzoate (INCI: Ethylhexyl salicylate).

Preferably, according to the process chosen, in a third or fourth process step, the organopolysiloxane gel of the invention obtained after the first or second or optional third process step is homogenized using standard high-shear mixing techniques until the consistency is creamy. Technologies suitable for the purpose are the same as mentioned above for the dilution step. When an additional amount of diluent has been added in the optional third process step, it is distributed homogeneously in the gel in the fourth process step. The gel swells and its softness changes.

"Creamy" in relation to the gel is understood to mean that the starting gel can be sheared until the consistency is creamy. The resulting creamy gel, according to its nature, may be pourable or comparatively stiff. The attribute "creamy" distinguishes these sheared gels, which may be transparent or opaque, from the gels produced directly by gelation of the reactive constituents.

"Storage-stable" in the context of this invention is understood to mean that the organopolysiloxane gels formed do not separate into two or more phases within 6 months of storage at room temperature. There is preferably no change in the softness of the gel within this period.

The person skilled in the art will understand that the absorption capacity for diluents is generally limited because of the three-dimensional network structure of organopolysiloxane gels and can vary depending on the network structure and network composition. If the absorption capacity for diluents has been exceeded, the formation of a diluent phase in addition to a gel phase is apparent.

The organopolysiloxane gels of the invention are suitable with particular preference for cosmetic applications, and are therefore preferably used in cosmetic compositions. However, they are also suitable for other applications, for example for medical and industrial applications.

The organopolysiloxane gels are of particular value in personal care products. They can be distributed gently on the skin and can therefore be used alone or mixed with other personal care product constituents, in order to form a multitude of personal care products.

Examples of personal care product constituents are esters, waxes, oils and fats of animal or vegetable origin, fatty alcohols, fatty acids, alkyl esters of fatty acids, hydrocarbons and hydrocarbon waxes, water, organic solvents, perfumes, surfactants, oil-soluble vitamins, water-soluble vitamins, oil-soluble medicaments, water-soluble medicaments, UV absorbers and active pharmaceutical compounds.

More particularly, the organopolysiloxane gels of the invention are suitable for antiperspirants and deodorants, since they leave a dry feel and do not cool the skin down during evaporation. They are glidable and improve the properties of skin creams, skincare lotions, moisturizers, face treatments, for example acne or wrinkle removers, body and face cleansers, bath oils, perfumes, eau de cologne, sachets, sunscreens, preshave and aftershave lotions, liquid soaps, shaving soaps and shaving foams. They can be used in hair shampoos, hair conditioners, hair sprays, mousses, permanent wave compositions, hair removers and cuticle removers, in order to improve shine and dry gliding and to provide conditioning benefits.

In cosmetics, they function as distributing agents for pigments in makeup, color cosmetics, foundation, rouge, lipsticks, lipbalm, eyeliner, mascara, grease removers and color cosmetic removers. They are suitable as administration systems for oil-soluble active constituents mentioned herein by way of example, for example vitamins, medicaments and UV absorbers. When they are used in sticks, gels, lotions, creams, roll-ons, the elastomers impart a dry, silky-smooth feel. Incorporated into cosmetics and other skincare products, the elastomers impart a matting effect.

In addition, the organopolysiloxane gels exhibit a multitude of advantageous properties, for example clarity, storage stability and simplicity of production. Therefore, they have a wide range of application, especially in antiperspirants, deodorants, skincare products, in perfumes as carriers and for hair conditioning, for example in hair balm or hair mask conditioners.

The organopolysiloxane gels have uses outside the personal care sector, including the use thereof as filler or insulation material for electrical cables, soil or water barriers for soil stabilization, or as a substitute for epoxy materials which are used in components in the electronics industry. They are likewise suitable as carriers for crosslinked silicone rubber particles. In these applications, they (i) allow simplicity of introduction of particles into such silicone phases or organic phases, such as sealants, paints, coatings, greases, adhesives, antifoams and casting resin compounds, and (ii) provide modified rheological, physical or energy-absorbing properties of such phases, either in their pure state or in their final state.

In addition, the organopolysiloxane gels are capable of acting as carriers for pharmaceuticals, biocides, herbicides, pesticides and other biologically active substances.

In addition, the compositions are employed as additives for nonwoven cellulose-based carrier substrates or nonwoven synthetic carrier substrates which are used in moist cleansing tissues such as moist tissues, moist paper towels and moist hand towels, which are generally marketed for personal hygiene and domestic cleaning purposes.

The organopolysiloxane gels of the invention can be used as carriers for controlled and easily regulated release of a volatile active organic substance into the free atmosphere when they are mixed therewith. The volatile substance may especially be a perfume or an insecticide or a substance that repels insects.

In this use, the organopolysiloxane gels of the invention find wide use, for example in the modification of fibers, textiles and materials made from cotton or synthetic fibers, woven fabrics, towels, including paper towels, toilet paper or wiping paper, such as serviettes or kitchen roll, or nonwoven fabric, for long-lasting controlled fragrancing or insect repulsion. The mixture of the organopolysiloxane gel of the invention and the volatile active organic substance can also be applied in washing machines and laundry driers directly to materials and textiles as such or as an addition to washing compositions and fabric softeners.

The use of the organopolysiloxane gels of the invention as carriers for controlled and easily regulated release of a volatile active organic substance finds use especially in the abovementioned cosmetic applications, where they can achieve an additional effect to the effect described above, by releasing, for example, a perfume in a controlled manner. The organopolysiloxane gels of the invention can also be used in insect repellent preparations, where they release an insecticide or a substance that repels insects. Such products can, for example, be applied directly to the skin or the clothing.

In a further application, the mixture of the organopolysiloxane gel of the invention and the volatile active organic substance can be used for controlled fragrancing or insect repulsion in closed spaces, for example in living spaces, offices, bathrooms or motor vehicles such as buses and cars.

EXAMPLES

The examples which follow serve to further illustrate the invention and describe its function and use in practice. In this regard, they should be considered to be illustrative and not restrictive.

The examples state physical parameters that have been determined by the test methods described hereinafter. If there are no details in the example text as to the exact traceability of measurement, these are already given in the descriptions of the test methods that follow here. In other words, in this case, further details are considered to be those given in the texts for the test methods.

Analytical Methods

The viscosity of the organopolysiloxane gels was determined in accordance with DIN EN ISO 3219 at a shear rate of 1/s and 25° C.

The viscosity of the organopolysiloxanes, such as Si—H-containing crosslinkers, organopolysiloxane resins and polydimethylsiloxanes, was determined in accordance with DIN 53019 in the linear range at 25° C.

The iodine number was determined in accordance with DIN 53241-1 by the method according to Wijs.

Gel permeation chromatography to determine the weight-average molecular weight Mw was conducted in accordance with ISO 16014-1 and ISO 16014-3.

The organopolysiloxane gels of the invention result in sensory advantages in cosmetic applications in that they improve the distributability of the product on the skin and impart a silky-smooth feel to the product. The organopolysiloxane gels are comparable in terms of their performance only when they are adjusted to a uniform viscosity for sensory testing. A particularly advantageous viscosity for this purpose has been found to be in the range of 75,000-120,000 mPas at 25° C. A criterion for the successful production of the organopolysiloxane gels is therefore the possibility of establishing this viscosity corridor. If this is not possible, there is no comparability with the other organopolysiloxane gels. It is a particular characteristic of the process of the invention that it permits the establishment of a target viscosity, such as 75,000-120,000 mPas here, independently of the process with retention of the sensory properties. This is demonstrated in the examples which follow and this property is delimited from the rest of the prior art.

The sensory properties of the organopolysiloxane gels described in the examples below were assessed by a trained group of 5 testers (panelists).

The panelists applied 0.05 g in each case of the product to the cleaned lower arm over a circular area of 20 cm², and the organopolysiloxane gels were compared with respect to their distributability relative to one another. The application was effected with the index finger or middle finger and a speed of rotation of two revolutions per second. A total of 30 revolutions were conducted. After a wait time of 60 seconds, the residues of the organopolysiloxane gels were compared with respect to their silkiness relative to one another.

Relative direct comparability is always possessed here solely by the organopolysiloxane gels that have been produced using the same or at least an equivalent diluent, i.e. more particularly with a volatile or nonvolatile diluent. Since different diluents result in different behavior on application and in terms of the residue, products having different diluents have to be assessed separately from one another in each case.

Example 1 (Inventive)

A 2000 mL glass reaction vessel is equipped with a condenser with attached nitrogen inlet, heating mantle, anchor stirrer and closed-loop temperature controller. The reaction vessel is charged with 497 g of a linear trimethylsilyl-terminated polydimethylsiloxane having a viscosity of 5 mPas at 25° C. Thereafter, 82 g of short-chain Si—H-containing polydimethyl-siloxane number 14 from table 1 (chain length 140) and 20 g of long-chain Si—H-containing polydimethylsiloxane number 28 from table 2 (chain length 450) are added.

Then 109.55 g of a 50% solution of an MQ resin ($M/M^{vi}/Q=7.6/1/11.4$; $M_n=2570$, $M_w=5440$, iodine number=18; $M=Me_3SiO_{1/2}$, $M_{vi}=Me_2ViSiO_{1/2}$, $Q=SiO_{4/2}$ with Me=methyl radical and Vi=vinyl radical) in the same linear trimethylsilyl-terminated polydimethylsiloxane having a viscosity of 5 mPas at 25° C. which is also used as diluent are added. Lastly, 0.7 g of a mixture of platinum 1,3-divinyl-1,1,3,3-tetramethyldisiloxane complex in divinyltetra-methyldisiloxane is added, with adjustment of the mixture such that the amount added corresponds to 52 ppm by weight of Pt, based on the sum total of the mass of the MQ resin and the two Si—H-containing organopolysiloxanes. The reaction vessel is closed and purged with nitrogen for 5 min.

Subsequently, the reaction mixture is heated to 95° C. at a stirrer speed of about 200 rpm, employing a heating rate of 45° C./h. Gel formation takes place within 30 minutes after the internal temperature of 95° C. has been attained. On completion of gel formation, the heating is switched off and the mixture is stirred for a further 60 minutes.

Thereafter, 5.83 g of polydimethylsiloxane having 3-mercaptopropyl groups and a viscosity of 190 mPas at 25° C. and a mercaptan content (SH content) of 0.29% by weight are added as stopper. The amount of mercaptan that was added in this way corresponds to 108 ppm by weight, based on the total amount of Si—H-containing organopolysiloxanes and MQ resin, and is thus more than twice as large as the amount of platinum used.

In addition, 89.68 g of the polydimethylsiloxane used as diluent having a viscosity of 5 mPas at 25° C. are added, and the stopper and the further diluent are stirred in while tilting by an ULTRA-TURRAX® T 50 at 6000 rpm for 5 minutes. This operation is repeated twice more with the same amount of diluent each time. No further stopper is added here. In this way, a creamy, transparent gel with very smooth consistency is obtained, which is suitable for use in cosmetic products.

The solids content, i.e. the total content of network of MQ resin and the two Si—H-containing organopolysiloxanes, and also the stopper and the catalyst in the diluent, after dilution is 16% by weight.

The organopolysiloxane gel obtained has a viscosity of 117,000 mPas at 25° C.

According to the assessment by the panelists, the organopolysiloxane gel obtained has very good distributability.

The residue was classified as plentiful and by the majority as predominantly silky and velvety.

Example 2 (Inventive)

The procedure corresponds to that described in example 1, with the difference that, in example 2, rather than the nonvolatile linear diluent, volatile decamethylpentacyclosiloxane is used as diluent.

After diluting to a solids content of 16% by weight, the viscosity is 152,000 mPas at 25° C.

According to the assessment by the panelists, the organopolysiloxane gel obtained has very good distributability. The residue was classified as plentiful and by the majority as dry, silky and velvety.

Example 3 (Inventive)

The procedure corresponds essentially to that described in example 1. By contrast with example 1, the diluent used, rather than a nonvolatile trimethylsilyl-terminated linear polydimethylsiloxane having a viscosity of 5 mPas at 25° C., is a volatile trimethylsilyl-terminated linear polydimethylsiloxane having a viscosity of 2 mPas at 25° C. The amount of diluent initially charged in the reaction vessel is 425.0 g. Rather than short-chain Si—H-containing polydimethylsiloxane number 14 from table 1, 67.75 g of short-chain Si—H-containing polydimethylsiloxane number 11 from table 1 (chain length 75) are weighed in and 20.0 g of long-chain Si—H-containing polydimethylsiloxane number 28 from table 2 (chain length 450) are added. 100.0 g of the same MQ resin formulation as used in example 1 are added. Lastly, 3.0 g of a mixture of platinum 1,3-divinyl-1,1,3,3-tetramethyldisiloxane complex in divinyltetramethyldisiloxane diluted with the trimethylsilyl-terminated polydimethylsiloxane having viscosity 2 mPas at 25° C. are added, with adjustment of the mixture such that the amount added corresponds to 26 ppm by weight of Pt, based on the sum total of the mass of the MQ resin and the two Si—H-containing polydimethylsiloxanes.

The further procedure corresponds to that described in example 1. For stopping, 2.0 g of polysiloxane having 3-mercaptopropyl groups and a viscosity of 190 mPas at 25° C. and a mercaptan content (SH content) of 0.29% by weight are added as stopper. The amount of mercaptan that was added in this way corresponds here to 42 ppm by weight, based on the total amount of Si—H-containing polydimethylsiloxanes and MQ resin, and thus corresponds to 1.6 times the amount of platinum used. This base gel is then diluted by adding 57.75 g of further diluent in the first dilution step, 67.54 g in the second step and 104.3 g in the third step. The procedure in the dilution corresponds to the same as described in example 1.

The final solids content, i.e. the content of network formed from the Si—H-containing polydimethylsiloxanes and the MQ resin together with the amount of catalyst used and the stopper oil, is 16% by weight. The following viscosities were measured during the dilution:

Before the first dilution: solids content: 22.5%: 344,000 mPas

After the first dilution: solids content: 20.5%: 258,000 mPas

After the second dilution: solids content: 18.5%: 169,000 mPas

After the third dilution: solids content: 16%: 91,400 mPas

According to the assessment by the panelists, the organopolysiloxane gel obtained has very good distributability. The residue was classified as plentiful and by the majority as dry, silky and velvety.

Example 4 (Inventive, in a Two-Stage Process)

The procedure corresponds to that of example 1, except that the hydrosilylation here is run in two stages. Firstly, the short-chain Si—H-containing polydimethylsiloxane is hydrosilylated on its own, then the long-chain Si—H-containing polydimethylsiloxane is hydrosilylated. The solvent used here, rather than the nonvolatile trimethylsilyl-terminated polydimethylsiloxane having a viscosity of 5 mPas from example 1, is decamethylcyclopentasiloxane. Moreover, in this example, there is no subsequent dilution, but addition of the total amount of diluent required from the start.

A 2000 mL glass reaction vessel is equipped with a condenser with attached nitrogen inlet, heating mantle, anchor stirrer and closed-loop temperature controller. The reaction vessel is charged with 446.4 g of decamethylcyclopentasiloxane. Thereafter, 62.5 g of a 50% solution of an MQ resin (M/M$^{vi}$/Q=7.6/1/11.4, $M_n$=2570, $M_w$=5440, iodine number=18), as described in example 1, in a nonvolatile linear trimethylsilyl-terminated polydimethylsiloxane having a viscosity of 5 mPas at 25° C. are added, followed by 46.8 g of short-chain Si—H-containing polydimethylsiloxane number 14 from table 1 (chain length 140). Lastly, 0.4 g of a mixture of platinum 1,3-divinyl-1,1,3,3-tetramethyldisiloxane complex in divinyltetramethyldisiloxane is added, with adjustment of the mixture such that the amount added corresponds to 51 ppm by weight of Pt, based on the sum total of the mass of the MQ resin and the two Si—H-containing polydimethylsiloxanes. Only the short-chain Si—H-containing polydimethylsiloxane was added here at first, but the amount of platinum is already calculated for the sum total of the amount of both Si—H-containing polydimethylsiloxanes. The reaction vessel is closed and purged with nitrogen for 5 min.

Subsequently, the reaction mixture is heated to 95° C. at a stirrer speed of about 200 rpm, employing a heating rate of 45° C./h. Gel formation takes place within 30 minutes after the internal temperature of 95° C. has been attained. On completion of gel formation, stirring is continued at internal temperature 95° C. for one hour.

Then 11.7 g of long-chain Si—H-containing polydimethylsiloxane number 28 from table 2 (chain length 450) are metered in and the mixture is stirred at 95° C. for a further hour. After this time, gel formation is complete.

Thereafter, 3.24 g of polysiloxane having 3-mercaptopropyl groups and a viscosity of 190 mPas at 25° C. and a mercaptan content (SH content) of 0.29% by weight are added as stopper. The amount of mercaptan that was added in this way corresponds to 104 ppm by weight, based on the total amount of Si—H-containing polydimethylsiloxanes and MQ resin, and is thus twice as large as the amount of platinum used.

The gel obtained has a solids content of 16% by weight and has a viscosity of 98,000 mPas at 25° C.

According to the assessment by the panelists, the organopolysiloxane gel obtained has very good distributability. The residue was classified as plentiful and by the majority as silky and velvety.

Comparative Example 1

Noninventive, Solely Short-Chain Si—H-Containing Organopolysiloxane, High Heating Rate The procedure corresponds essentially to that described in example 1:

By contrast with example 1, solely an Si—H-containing polydimethylsiloxane is used, which is short-chain Si—H-containing polydimethylsiloxane number 14 from table 1 (chain length 140, a:b=50:1). 102.4 g thereof are used.

In this example, the heating rate is set to 90° C./h. Such a high heating rate is easy to achieve in the laboratory on this scale, but industrially at a size of 1 m$^3$ or more is no longer possible, even when working with high-pressure steam. Moreover, there is the risk of significant local overheating that leads to drying-out of the gel at these sites and irreversible particle formation that destroys the sensory properties of the gel.

A gel is obtained with a solids content of 16% by weight and a viscosity of 108,000 mPas at 25° C.

According to the assessment by the panelists, the organopolysiloxane gel obtained has very good distributability. The residue was classified as plentiful and by the majority as predominantly silky and velvety.

Comparative Example 2

Noninventive, Analogous to Comparative Example 1, but with Lower Heating Rate The procedure corresponds to that of comparative example 1 except that heating is now at a heating rate of 45° C./h. The product does not attain the consistency of a gel, but remains free-flowing, and its properties correspond more to those of an oil. In an attempt to test it, it runs of its own accord even prior to manual distribution on the skin.

By contrast with comparative example 1, what it leaves is not a matt, silky film but an oily, shiny layer, which has not been assessed as silky by any of the panelists.

It is unsuitable for use in cosmetic products since it does not have a suitable consistency and does not have suitable sensory properties.

The process in its composition according to comparative example 1, owing to its sensitivity to the heating rate, in the given composition, cannot be increased from the laboratory scale (with a high heating rate) to the production scale of 1 m$^3$ or greater (with a lower heating rate).

Comparative Example 3

Noninventive, Analogous to Comparative Example 2 with Low Heating Rate but Longer-Chain Si—H-Containing Organopolysiloxane The procedure corresponds to that described in comparative example 2, except that the Si—H-containing organopolysiloxane used is long-chain Si—H-containing polydimethylsiloxane number 28 from table 2 (chain length 450, a:b=50:1) rather than the short-chain Si—H-containing organopolysiloxane. Only this one Si—H-containing polydimethylsiloxane is used.

An elastomer gel is obtained which, at a solids content of 16% by weight, has a viscosity of 205,000 mPas at 25° C. and which, at a solids content of 14% by weight, has a viscosity of 122,000 mPas at 25° C.

By contrast with comparative example 1, a very much higher viscosity is obtained at a desired solids content of 16% by weight. If the solids content is reduced to 14% by weight, only then is a comparable viscosity to that in comparative example 1 obtained. But both factors, the solids content and the viscosity, affect the sensory properties of the gel.

According to the assessment of the gel adjusted to 122 000 mPas by the panelists, the organopolysiloxane gel obtained has very good distributability. The residue was classified as plentiful and as silky and oily.

The gel obtained is suitable for production of cosmetic products, but has good sensory distinguishability from the corresponding gel from comparative example 1. In the direct comparison, 4 out of 5 panelists preferred the gel from comparative example 1 over this gel.

The test was then repeated with the same panelists, without telling them that they were comparing the same gels with one another again. In the repetition, 5 out of 5 panelists preferred the gel from comparative example 1 over this gel.

In the transfer from the laboratory scale with high heating rate to the production scale with low heating rate, on replacement of the short-chain Si—H-containing organopolysiloxane by the long-chain Si—H-containing organopolysiloxane, it is not possible to obtain an organopolysiloxane gel having comparable sensory properties.

Example 5

Inventive, Adjustment of the Amounts of Si—H-Containing Organopolysiloxanes to Altered Heating Rate, with Retention of the Same Properties of the Organopolysiloxane Gel The procedure corresponds to that described in example 1. By contrast with example 1, however, heating is now not at 45° C./h, but at 90° C./h, i.e. twice as high a heating rate is employed.

By contrast with example 1, the following amounts of the Si—H-containing polydimethylsiloxanes are now used:

92 g of Si—H-containing polydimethylsiloxane number 14 from table 1 (chain length 140) and 10 g of Si—H-containing polydimethylsiloxane number 28 from table 2 (chain length 450, a:b=50:1).

Otherwise, the experimental procedure corresponds exactly to that described in example 1. As a result, an organopolysiloxane gel having a viscosity of 121,000 mPas is obtained at a solids content of 16% by weight.

According to the assessment by the panelists, the organopolysiloxane gel obtained has very good distributability. The residue was classified as plentiful and by the majority as predominantly silky and velvety.

In the direct comparison test, 3 out of 5 panelists preferred the gel from example 1 over this gel from example 5. The comparison test was repeated with the same panelists, without telling them that they were comparing the same gels with one another again. In the repetition, 2 out of 5 panelists preferred the gel from example 1 over this gel from example 5, and only one of the two panelists who preferred the gel from example 1 in the repeat test already arrived at this result in the first test. There is therefore no certain distinguishability of the two gels from example 1 and from example 5 on the basis of their sensory properties.

This means that the two gels have virtually equivalent properties and the inventive use of two kinds of Si—H-containing organopolysiloxanes, a short-chain and a long-chain Si—H-containing organopolysiloxane, permits adjustment to altered boundary conditions, such as change in the heating rate, with retention of the desired properties of the organopolysiloxane gel, which would not be possible with use of just one kind of Si—H-containing organopolysiloxane, solely a short-chain or solely a long-chain Si—H-containing organopolysiloxane.

The invention claimed is:

1. A process for producing organopolysiloxane gels, comprising:
reacting
(1a) unsaturated organopolysiloxane resins comprising units of the formulae $SiO_2$(Q units) and $R_3SiO_{1/2}$ and $R_2R^1SiO_{1/2}$(M units), where
R each independently is a monovalent, optionally substituted hydrocarbon radical having 1 to 18 carbon atoms per radical,
$R^1$ each independently is a monovalent hydrocarbon radical onto which Si-H groups are optionally added in a hydrosilylation reaction,
with the proviso that the organopolysiloxane resins contain at least 2 $R^1$ radicals, and that the molar ratio of M units to Q units is in the range from 0.5 to 4.0, the organopolysiloxane resins optionally containing, in addition to the M and Q units, small amounts of $RSiO_{3/2}$ (T) units and/or $R_2SiO_{2/2}$ (D) units, in amounts of 0.01 to 20 mol %, based on the sum total of all siloxane units, the organopolysiloxane resins optionally containing up to 10% by weight of Si-bonded hydroxyl or alkoxy groups,
and optionally
(1b) compounds having a polar organic group and a hydrosilylatable end group, with
(2) a mixture of two Si-H-containing organopolysiloxanes which have different average chain lengths, of the formula:

  (I)

where $R^2$ each independently is an unsubstituted or optionally heteroatom-substituted, aliphatic, cycloaliphatic or aromatic, optionally polycyclic, $C_1$-$C_{18}$ hydrocarbon radical, x is 0 or 1,
a and b are each integers ≥0,
with the provisos that the sum total of a+b ≥30, that the organopolysiloxanes contain an average of at least 2 Si-bonded hydrogen atoms, and that the long-chain organopolysiloxane has at least 3 times the chain length (a+b) of the short-chain organopolysiloxane,
in the presence of
(3) catalysts that promote the addition of Si-bonded hydrogen onto aliphatic multiple bonds,
where (1a), optionally (1b) and (2) is/are dispersed in (4) diluents
and the reaction is stopped by addition of
(5) stopper compounds used as catalyst poisons.

2. The process of claim 1, wherein x=0 in formula (I).

3. The process of claim 1, wherein the sum of a+b >55 in the formula (I).

4. The process of claim 1, wherein catalysts (3) are metal catalysts in amounts of 1 to 100 ppm by weight (parts per weight per million parts by weight), calculated as elemental metal, based in each case on the total weight of components (1a), optionally (1b) and (2).

5. The process of claim 1, wherein at least one diluent (4) is a polydimethylsiloxane having 2 to 50 silicon atoms, an aliphatic or alicyclic hydrocarbons having 4 to 30 carbon atoms, or an ester of a carboxylic acid having 2 to 30 carbon atoms.

6. The process of claim 1, wherein at least one stopper compound (5) is an organic compound having mercapto groups (SH) or an organopolysiloxane having mercaptoalkyl groups.

7. The process of claim 1, wherein the stopper compounds (5) are used in amounts of at least 1.1 mol of functional group that brings about the stopping per mole of elemental metal.

8. The process of claim 1, wherein the organopolysiloxane gels obtained after the reaction are homogenized to obtain organopolysiloxane gels which do not separate into two or more phases in the course of storage at room temperature (20° C.) for six months.

9. The process of claim 1, wherein the organopolysiloxane gels obtained are diluted with further diluents (4) and/or active ingredients for personal care or healthcare and then optionally homogenized.

10. A cosmetic composition comprising an organopolysiloxane gel produced according to claim 1.

* * * * *